United States Patent

Raspanti et al.

Patent Number: 5,759,525
Date of Patent: Jun. 2, 1998

[54] CONCENTRATED SOLUTIONS OF A 1,3,5-TRIAZINE DERIVATIVE SUNSCREEN AND THEIR USE FOR THE PREPARATION OF COSMETIC COMPOSITIONS

[75] Inventors: Giuseppe Raspanti; Alverio Malpede, both of Bergamo, Italy

[73] Assignee: 3V Inc., Weehawken, N.J.

[21] Appl. No.: 772,873

[22] Filed: Dec. 26, 1996

[51] Int. Cl.$^6$ ............... A61K 7/42; A61K 7/00; A61K 31/53; C07D 251/70
[52] U.S. Cl. .............. 424/59; 424/400; 424/401; 514/245; 544/197
[58] Field of Search ............... 424/59, 60, 400, 424/401; 514/245; 544/197

[56] References Cited

U.S. PATENT DOCUMENTS

| | | | |
|---|---|---|---|
| 4,617,390 | 10/1986 | Hoppe et al. | 544/197 |
| 4,978,523 | 12/1990 | Motegi et al. | 424/59 |
| 5,346,691 | 9/1994 | Raspanti | 424/59 |

Primary Examiner—Shelley A. Dodson
Attorney, Agent, or Firm—Griffin, Butler, Whisenhunt & Szipl

[57] ABSTRACT

It is disclosed a solution consisting of from 15 to 60% by weight of a compound of formula (I)

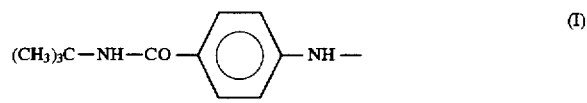

(I)

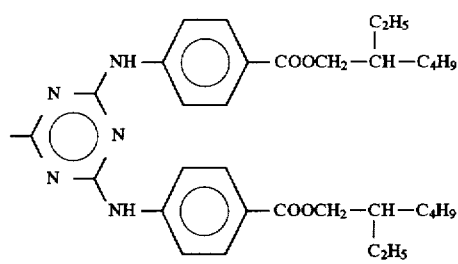

and from 40 to 85% by weight of at least an ester of formula (II)

$$A\text{-}(COO\text{-}B)_n \qquad (II)$$

wherein:

n is the number 1 or 2;

A, when n is 1, is a $C_6$–$C_{20}$ straight or branched alkyl group, phenyl, optionally substituted with one or more $C_1$–$C_4$ straight or branched alkyl groups, hydroxy, $C_1$–$C_4$ straight or branched alkoxy, or when n is 2, A is a saturated or unsaturated $C_2$–$C_{12}$ alkylene chain, optionally substituted with one or more hydroxy groups or A is a phenylene group.

B is a $C_3$–$C_{18}$ straight or branched alkyl group; $C_5$–$C_{12}$ cycloalkyl optionally substituted with one or more $C_1$–$C_4$ straight or branched alkyl groups. Said solution is useful for the preparation of sun protecting cosmetic compositions as well as for their stabilization against photoinduced degradation.

12 Claims, No Drawings

CONCENTRATED SOLUTIONS OF A 1,3,5-TRIAZINE DERIVATIVE SUNSCREEN AND THEIR USE FOR THE PREPARATION OF COSMETIC COMPOSITIONS

The present invention relates to concentrated solutions of lipophilic suncreens derivatives of 1,3,5-triazine and in particular to a method for their solubilization in solvents suitable for the preparation of cosmetic compositions.

BACKGROUND OF THE INVENTION

It is well known that sun radiations ranging from 290 to 400 nm are noxious to organic materials, among which cutaneous tissue too. In fact, continuous exposition to sun radiations is considered the main cause of the development of degenerative processes and of skin cancer forms.

In particular, radiations with a wavelength between 290 and 320 nm, so-called UV-B radiations, are the cause of erythema and sunburns, whose severity depends on the duration of exposition.

By means of the use of particular compounds, so called sunscreens, which are capable of absorb, at least partially, sunlight UV radiations, or of formulations containing these compounds it is possible to avoid or at least attenuate the noxious effects and slow down human skin ageing.

As protective agents, a number of substances have been studied and tested and with regard to this a wide patent literature exists, disclosing several compounds, belonging to different chemical classes and capable of absorbing in the UV range of sun radiation, particularly in that comprised between 290 and 390 nm.

For the protection of the skin from sunburns and erythema caused by UV-B radiation, different compounds, such as for example derivatives of cinnamic acid, 4-aminobenzoic acid, benzylidencamphor, benzophenone, diphenylcyanoacrylic acid, s-triazine are known, and widely used in cosmetic compositions.

Among the derivatives of s-triazine, particularly interesting are the suncreens described in the U.S. Pat. No. 5,346,691. In fact, these compounds, other than a high extinction coefficient in UV-B, therefore an optimal efficacy, show also a very high solubility in most of the solvents used in cosmetics for the preparation of sunscreen compositions.

For the photoprotection of the skin, many compositions have been proposed, and also with regard to this a vast patent literature exists.

Very often, these sunscreen compositions are in the form of an oil-in-water emulsion containing, in variable concentrations, one or more lipophilic and/or hydrophilic organic sunscreens, capable of absorbing more or less intensely sunlight UV radiations.

The kinds of sunscreens and the amounts for their use are selected depending on the desired sun protecting factor (SPF). SPF is an index of protection and is expressed as the ratio between the time of irradiation necessary to reach the erythematogenic threshold in the presence of the UV filter and the time necessary to reach the erythematogenic threshold in the absence of the UV filter. SPF can be determined according to the method described by B. Diffey and J. Robson in J. Soc. Cosmet. Chem. 40, 127–133 (1989).

Among the sunscreens described in U.S. Pat. No. 5,346,691, particularly suitable for the use in the preparation of sunscreen composition is the compound of the following formula (I):

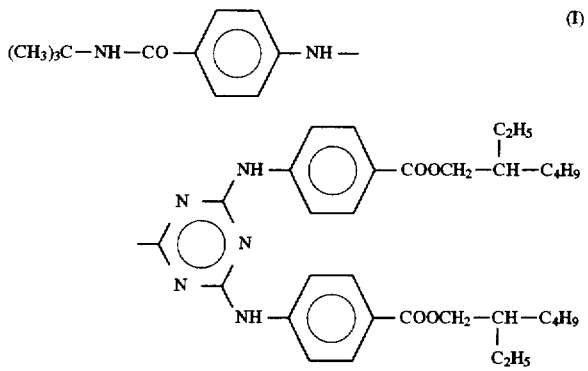

This compound is in the form of a white solid, it has a very high activity in UV-B and has a very high solubility in the solvents commonly used in the formulation of sunscreen compositions.

Some cosmetics manufacturers find some drawbacks in using the solid form of the sunscreen. These drawbacks consists in the troublesome handling of a powder, in the operation of dissolving it in a suitable solvent and in the time necessary for this operation.

ABSTRACT OF THE INVENTION

It has now surprisingly been found that the above drawbacks can be avoided when the compound of formula (I) is provided in the form of a liquid concentrated solution in one or more solvents selected from the group consisting of esters of carboxylic acids.

It is an object of the present invention a solution consisting of from 15 to 60% by weight of a compound of formula (I)

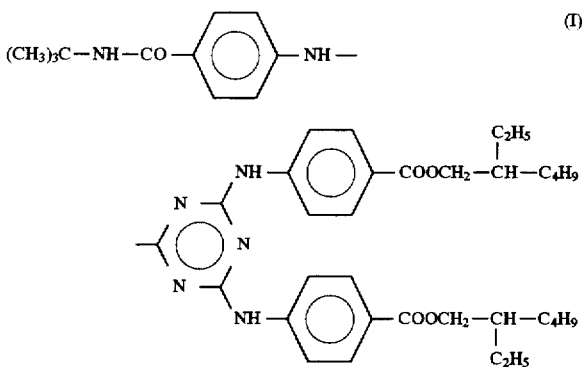

and from 40 to 85% by weight of a solvent consisting of at least an ester of formula (II)

wherein:

n is the number 1 or 2;

A, when n is 1, is a $C_6$–$C_{20}$ straight or branched alkyl group, phenyl optionally substituted with one or more $C_1$–$C_4$ straight or branched alkyl groups, hydroxy, $C_1$–$C_4$ straight or branched alkoxy, or when n is 2, A is a $C_2$–$C_{12}$ saturated or unsaturated alkylene chain, optionally substituted with one or more hydroxy groups or A is a phenylene group;

B is a $C_3$–$C_{18}$ straight or branched alkyl group; $C_5$–$C_{12}$ cycloalkyl optionally substituted with one or more $C_1$–$C_4$ straight or branched alkyl groups.

It is another object of the present invention a method for the preparation of said solution.

It is a further object of the present invention a method for the preparation of sun protecting cosmetic compositions comprising the addition of said solution to a cosmetic substrate. The cosmetic compositions containing said solution are also an object of the present invention.

These and other objects of the present invention will be disclosed in detail in the following disclosure and examples.

DETAILED DISCLOSURE OF THE INVENTION

According to the present invention, examples of $C_6$–$C_{20}$ straight or branched alkyl are hexyl, heptyl, octyl, dodecyl, tetradecyl, hexadecyl, octadecyl and their isomers, in particular 2-ethylpentyl, heptadecyl, pentadecyl, tridecyl are preferred.

Examples of $C_2$–$C_{12}$ alkylene chain are ethylene, trimethylene, tetramethylene, hexamethylene, decamethylene, in particular 1-hydroxyethylene and ethene is preferred.

Examples of optionally substituted phenyl are phenyl, toluyl, xylyl, trimethylphenyl, ethylphenyl, isopropylphenyl, terbutylphenyl, hydroxyphenyl, methoxyphenyl, ethoxyphenyl, propoxyphenyl, butoxyphenyl, and their isomers, in particular phenyl and 2-hydroxyphenyl are preferred.

Examples of $C_3$–$C_{18}$ straight or branched alkyl are propyl, butyl, pentyl, hexyl, octyl, decyl, tridecyl, pentadecyl, hexadecyl, octadecyl and their isomers.

Examples of cycloalkyl are cyclopentyl, cyclohexyl, 4-ter-butylcyclohexyl, menthyl.

Preferred solvents of formula (II) are: 2-ethylhexyl 2-ethylhexanoate, 2-ethylhexyl stearate, 2-ethylhexyl palmitate, bis(2-ethylhexyl) malate, isopropyl myristate, isopropyl palmitate, $C_{12}$–$C_{15}$ alkyl benzoate, menthyl salicylate, 2-ethylhexyl salicylate, bis n-octyl maleate, bis n-octyl fumarate.

In a preferred embodiment of the present invention, the solution consists of 20–50% by weight of the compound of formula (I) and of 80–50% by weight of at least a solvent of formula (II).

The solution according to the present invention is, so to say, ready for use, of simple dosage and use, since it avoids the handling of the substance in the powdery form and its dissolution, therefore significantly facilitating the task of the cosmetic manufacturer.

According to the present invention it is provided a method for the preparation of the above described solution. Said process comprises the addition of a suitable amount of the compound of formula (I) to the solvent under stirring, at a temperature ranging from 0° to 200° C., preferably from 20° to 180° C.

Alternatively, the solution can be prepared by adding the suitable amount of solvent to the compound of formula (I) in the melted state at a temperature ranging from 110° to 180° C.

The solvents of formula (II) used for the preparation of the solutions according to the present invention are esters of mono- or dicarboxylic acids, commercially available and commonly used and in any case preparable with methods well-known in literature.

The solutions object of the present invention are useful for the preparation of cosmetic compositions. Such compositions are suitable for the treatment and therefore the photoprotection of skin, of hair or make-up in the decorative cosmetic. A method for protecting human skin or hair from ultraviolet radiations consists in applying on the skin or hair a suitable amount of a cosmetic composition containing a solution of the present invention. A suitable amount shall be determined directly by the person using the composition or by an expert suggesting a suitable amount depending on the SPF of the composition, the kind of skin or hair to be protected and the radiation intensity.

According to the present invention, the cosmetic compositions can be solutions, lotions, emulsions of the water-in-oil or oil-in-water type; or can also be in the form of gels, lipsticks, aerosols.

The compositions according to the present invention are prepared by formulating the ingredients usually employed, such as for example oils, fats, emulsifiers, humectant agents, moisturizing agents, emollients, preservatives, surfactants, thickening agents, perfumes, pigments, dyes and other else such as alcohols, polyols, electrolytes, siliconic derivatives.

The more commonly used solvents are natural or synthetic triglycerides, hydrocarbons, esters of fatty acids with isopropanol, propylene glycol, glycerin, or fatty alcohols, propylene glycol monomethyl- or monoethyl- or monobutylether, dioctyl malate.

The present invention comprises also a method for the protection of the cosmetic compositions themselves from UV radiation by means of the addition of from 0.2 to 40.0%, preferably from 1 to 30%, by weight with respect to the composition of a photostabilizing mixture consisting of the above solution of the compound of formula (I). In this case it is a matter of compositions whose components can undergo unwanted light-induced degradation or colouring, as for example shampoos and hair lacquers, hair dressing lotions, hair-dyeing compositions, make-up formulations, as nail lacquers, foundation, lipstick. Preferred cosmetic formulations are the ones for the protection of skin from sun radiations. Therefore, also a method for stabilizing a cosmetic composition is a further object of the present invention.

On the other hand, the solution according to the present invention is also useful for the preparation of a composition suitable for the protection of skin from ultraviolet radiations, in particular UV-B, with wavelength ranging from 290 to 320 nm.

The cosmetic compositions of the present invention, other than the above described solution, can also contain other complementary sunscreens and particularly those with a maximum absorption from 320 to 380 nm. Well-known sunscreens which can be combined with the solution of the present invention are for example: 3-(4-methylbenzylidene) camphor, 2-ethylhexyl (4-dimethylamino)benzoate, 2-ethylhexyl (4-methoxy)cinnamate, 2-hydroxy-4-methoxybenzophenone, 2,4,6-trianilino-(p-carbo-2-ethylhexyloxy)-1,3,5-triazine, 4-(1,1-dimethylethyl)-4'-methoxydibenzoylmethane, 2-ethylhexyl 2-cyano-3,3-diphenylacrylate, salts of 2-phenylbenzimidazol-5-sulfonic acid, salts of 2-hydroxy-4-methoxybenzophenone-5-sulfonic acid, 1,4-di(3-methylbenzylidenecamphor-10-sulfonic) acid.

Other than the above described solution, the sun protecting compositions according to the present invention can also contain inorganic pigments commonly used in cosmetics, such as for example titanium dioxide, zinc oxide, silicon oxide or aluminium oxide.

The following examples further illustrate the invention:

EXAMPLE 1

100 g of compound of formula (I) were added, in a period of 15 minutes and under stirring, to 100 g of bis n-octyl maleate pre-heated to 70° C. Once the addition was finished, stirring was continued for 5 minutes, then the solution was cooled down to 20° C. and discharged, to obtain a pale yellow viscous solution.

EXAMPLE 2

100 g of compound of formula (I) were added, in a period of 30 minutes and under stirring, to 200 g of $C_{12}$-$C_{15}$ alkyl benzoate (Finsolv TN by the firm FINITEX) at room temperature. Once the addition was finished, stirring was continued for 2 hours, then the solution was discharged, to obtain a lightly yellow solution.

EXAMPLE 3

120 g of compound of formula (I) were added, in a period of 15 minutes and under stirring, to 80 g of isopropyl myristate pre-heated to 80° C. Once the addition was finished, stirring was continued for 10 minutes, then the solution was cooled to room temperature and discharged, to obtain a very viscous solution.

EXAMPLE 4

80 g of compound of formula (I) were added, in a period of 15 minutes and under stirring, to 120 g of menthyl salicylate pre-heated to 50° C. Once the addition was finished, stirring was continued for 30 minutes, then the solution was cooled to room temperature and discharged, to obtain a very viscous yellowish solution.

EXAMPLE 5

A suspension consisting of 200 g of Finsolv TN and 100 g of compound of formula (I) was slowly warmed under stirring to 90° C. Once the temperature of 90° C. was reached, stirring was continued for some minutes, then the solution was cooled to room temperature and discharged.

EXAMPLE 6

In a period of 5 minutes, 120 g of bis n-octyl maleate were added to 80 g of melted compound of formula (I), heated to 160° C.

Once the addition was finished stirring was continued for some minutes, then the solution was cooled and discharged.

EXAMPLE 7

In a period of 5 minutes, 110 g of a mixture consisting of 60 g of menthyl salicylate and 50 g of isopropyl myristate were added to 90 g of melted compound of formula (I), heated to 160° C. Once the addition was finished stirring was continued for 5 minutes, then the viscous solution was discharged.

EXAMPLE A—Lotion

| | |
|---|---|
| Solution of Example 1 | 5.0 g |
| Octyl octanoate | 48.0 g |
| Triglycerides $C_8$-$C_{10}$ | 34.5 g |
| Dioctylcyclohexane | 12.4 g |
| Perfume | 0.1 g |

The mixture was stirred for 10–15 minutes.

EXAMPLE B—O/W Sun cream

| | |
|---|---|
| $C_{12}$-$C_{15}$ Alkylbenzoate | 5.0 g |
| Diisopropyl adipate | 5.0 g |
| Shea butter | 2.0 g |
| α-Bisabalol | 0.5 g |
| 4-methoxy-4'-terbutyldibenzoylmethane | 2.5 g |
| Solution of Example 4 | 10.0 g |
| Stabylen 30 (R) (emulsifing agent by 3V SIGMA) | 0.3 g |
| Synthalen K (R) (Thickening agent by 3V SIGMA) | 0.3 g |
| Abiol (R) (Preservative by 3V SIGMA) | 0.3 g |
| Methylparaben | 0.2 g |
| Propylparaben | 0.1 g |
| Glycerine | 5.0 g |
| Aminomethylpropanol | 0.5 g |
| Water up to | 100.0 g |
| Perfume | |

The fatty phase was warmed to 70° C., sunscreens were added and stirring was done for 10–15 minutes. Stabylen 30 and Synthalen K were dispersed in water and the fatty phase was added under strong stirring to the 70° C. previously warmed aqueous dispersion. The resulting mixture was neutralized with aminomethylpropanol, cooled to 35° C. and preservatives, glycerine and perfume were added.

EXAMPLE C—O/W Day-cream

| | |
|---|---|
| Triglyceryl methylglucose distearate | 4.0 g |
| Glyceryl stearate | 1.0 g |
| $C_{12}$-$C_{15}$ Alkylbenzoate | 7.5 g |
| Avocado oil | 5.0 g |
| Diisopropyl adipate | 5.0 g |
| Solution of Example 3 | 3.0 g |
| 2-hydroxy-4-methoxybenzophenone | 2.0 g |
| Synthalen K (Thickening agent by 3V SIGMA) | 0.2 g |
| Abiol (R) (Preservative by 3V SIGMA) | 0.3 g |
| Methylparaben | 0.2 g |
| Propylparaben | 0.1 g |
| Aminoinethylpropanol | 0.15 g |
| Glycerine | 3.0 g |
| Water up to | 100.0 g |
| Perfume | |

Operations were performed as described in Example B.

EXAMPLE D—O/W Sun milk

| | |
|---|---|
| PEG-7 Hydrogenated castor oil | 7.5 g |
| Lanolin Alcohols in mineral oil | 2.5 g |
| Octyl octanoate | 7.5 g |
| Dioctylcyclohexane | 5.0 g |
| Cetylstearyl octanoate | 5.0 g |
| Solution of Example 1 | 6.0 g |
| Abiol (R) (Preservative by 3V SIGMA) | 0.3 g |
| Glycerine | 5.0 g |
| Water up to | 100.0 g |
| Perfume | |

The fatty phase was warmed to 70° C. and the sunscreens were added.

70° C. pre-heated water was added to the fatty phase under strong stirring. After cooling, preservative, glycerine and perfume were added.

EXAMPLE E—Lipstick

The base mixture was first prepared:

| Beeswax | 13.0 g |
|---|---|
| Carnauba wax | 7.5 g |
| Lanolin | 5.0 g |
| Isopropyl myristate | 8.0 g |
| Mineral oil | 3.0 g |
| Castor Oil | 63.5 g |

85 g of this mixture were warmed to melt. 20 g of the solution of example 2 and 7 g of 4-methoxy-4'-terbutyldibenzoylmethane as well as perfume and dyes were added to the molten mass, then it was diluted to 1000 g with castor oil and it was cooled at room temperature.

We claim:

1. A solution consisting of from 15 to 60% by weight of a compound of formula (I)

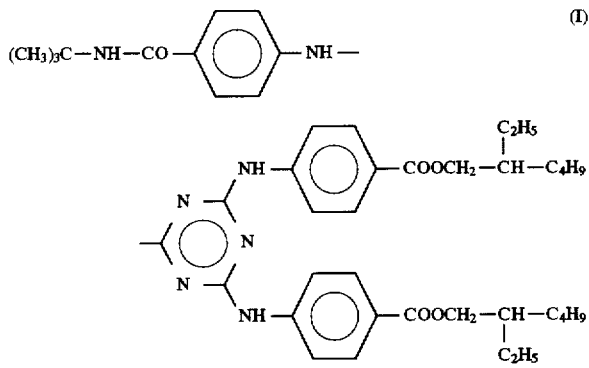

and from 40 to 85% by weight of a solvent consisting of at least an ester of formula (II)

wherein:
n is the number 1 or 2;
A, when n is 1, is a $C_6$–$C_{20}$ straight or branched alkyl group, phenyl optionally substituted with one or more $C_1$–$C_4$ straight or branched alkyl groups, hydroxy, $C_1$–$C_4$ straight or branched alkoxy, or
when n is 2, A is a saturated or unsaturated $C_2$–$C_{12}$ alkylene chain, optionally substituted with one or more hydroxy groups or A is a phenylene group;
B is a $C_3$–$C_{18}$ straight or branched alkyl group; $C_5$–$C_{12}$ cycloalkyl optionally substituted with one or more $C_1$–$C_4$ straight or branched alkyl groups.

2. A solution according to claim 1, consisting of 20–50% by weight of the compound of formula (I) and of 80–50% by weight of at least an ester of formula (II).

3. A solution according to claim 1, wherein the solvent is selected from the group consisting of: 2-ethylhexyl 2-ethylhexanoate, 2-ethylhexyl stearate, 2-ethylhexyl palmitate, bis(2-ethylhexyl) malate, isopropyl myristate, isopropyl palmitate, $C_{12}$–$C_{15}$ alkyl benzoate, menthyl salicylate, bis n-octyl maleate, 2-ethylhexyl salicylate, bis n-octyl fumarate and their mixtures.

4. A process for the preparation of the solution of claim 1, which comprises the addition of a suitable amount of the compound of formula (I) to the solvent under stirring, at a temperature ranging from 0° to 200° C.

5. A process for the preparation of the solution of claim 1, which comprises the addition of a suitable amount of solvent to the melted compound of formula (I) at a temperature ranging from 110° to 180° C.

6. A cosmetic composition containing from 0.2 to 40.0% by weight of a solution of claim 1.

7. A cosmetic composition according to claim 6, further containing one or more sunscreens selected from the group consisting of: 3-(4-methylbenzylidene)camphor, 2-ethylhexyl (4-dimethylamino)benzoate, 2-ethylhexyl (4-methoxy)cinnamate, 2-hydroxy-4-methoxybenzophenone, 2,4,6-trianilino-(p-carbo-2-ethylhexyloxy)-1,3,5-triazine, 4-(1,1-dimethylethyl)-4'-methoxydibenzoylmethane, 2-ethylhexyl 2-cyano-3,3-diphenylacrylate, salts of 2-phenylbenzimidazol-5-sulfonic acid, salts of 2-hydroxy-4-methoxybenzophenone-5-sulfonic acid, 1,4-di(3-methylbenzylidenecamphor-10-sulfonic) acid.

8. A cosmetic composition according to claim 6, selected from the group consisting of: lotion, oil-in-water sun cream, oil-in-water day-cream, water-in-oil sun milk and lipstick.

9. A cosmetic composition according to claim 6, further containing a component selected from the group consisting of: titanium dioxide, zinc oxide, silicon oxide and aluminium oxide.

10. A method for the stabilization of a cosmetic composition against the photoinduced degradation comprising the addition of from 0.2 to 40.0% by weight with respect to the total weight of the composition of the solution of claim 1.

11. A method for the protection of skin from ultraviolet radiation consisting in applying on the skin a suitable amount of a cosmetic composition according to claim 6.

12. A method for the protection of hair from ultraviolet radiation consisting in applying on the hair a suitable amount of a cosmetic composition according to claim 6.

* * * * *